United States Patent [19]

Ruiz

[11] 4,027,869

[45] June 7, 1977

[54] PATIENT RESTRAINT FOR X-RAY STUDIES OF INFANTS

[76] Inventor: Gilbert G. Ruiz, 2614 N. Sterling Drive, McHenry, Ill. 60050

[22] Filed: June 1, 1976

[21] Appl. No.: 691,566

[52] U.S. Cl. .............................................. 269/328
[51] Int. Cl.² ...................................... A61G 13/00
[58] Field of Search .................... 269/328; 128/134

[56] References Cited

UNITED STATES PATENTS

| 1,980,848 | 11/1934 | Cass ................................... | 269/328 |
| 2,460,308 | 2/1949 | Pribil ................................. | 269/328 |
| 2,675,564 | 4/1954 | Hughes ............................... | 128/134 |
| 3,358,141 | 12/1967 | Hoffmann et al. ................. | 128/134 |

Primary Examiner—Harold D. Whitehead
Assistant Examiner—Robert C. Watson
Attorney, Agent, or Firm—Darbo, Robertson & Vandenburgh

[57] ABSTRACT

Apparatus for immobilization of infant patients during exposure of X-ray film, particularly in connection with studies requiring the so-called frog-leg position. Use of this invention permits considerable reduction in the extent of exposure of the patient's body, and eliminates the need of manual restraint of extremities and exposure of a non-patient to radiation. Moreover, the required size of film is much reduced. In a preferred embodiment antero-posterior projections of a patient in both straight supine, and frog-leg positions are shown on a single 10 x 12 inch film. The invention virtually eliminates the need to re-expose because of movement of the patient.

3 Claims, 6 Drawing Figures

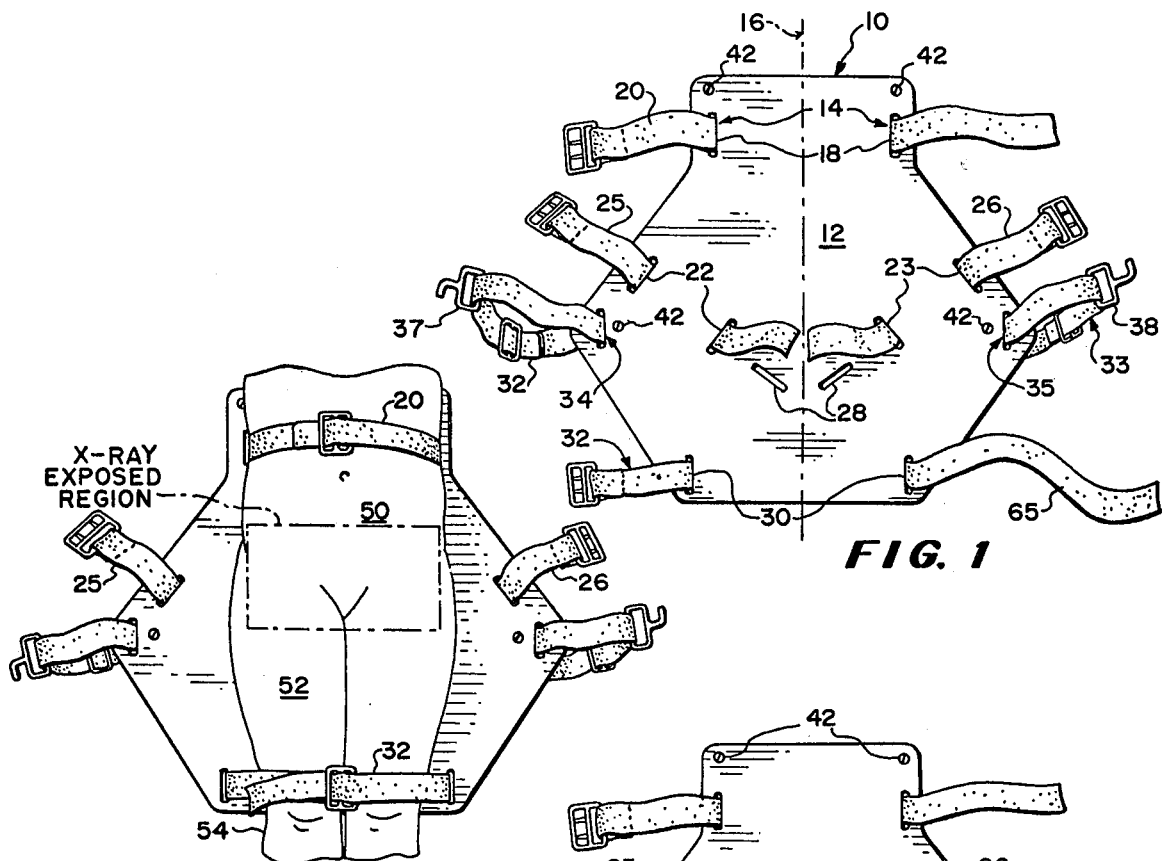
FIG. 1
FIG. 2
FIG. 3
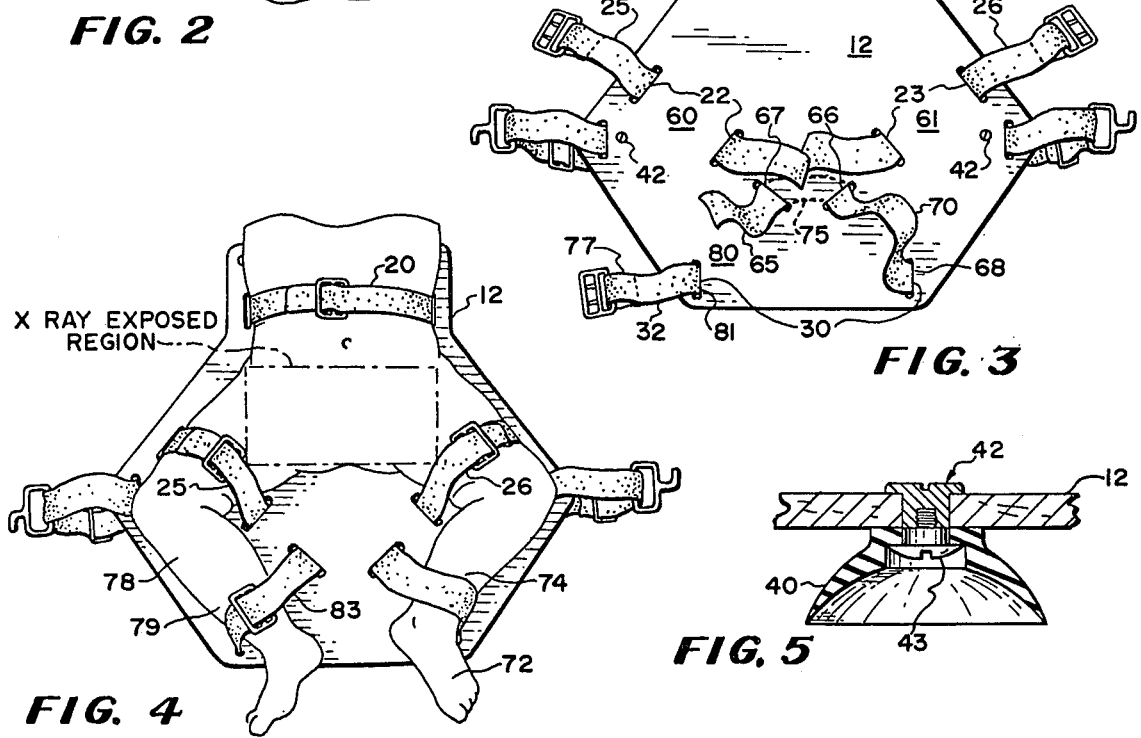
FIG. 4
FIG. 5

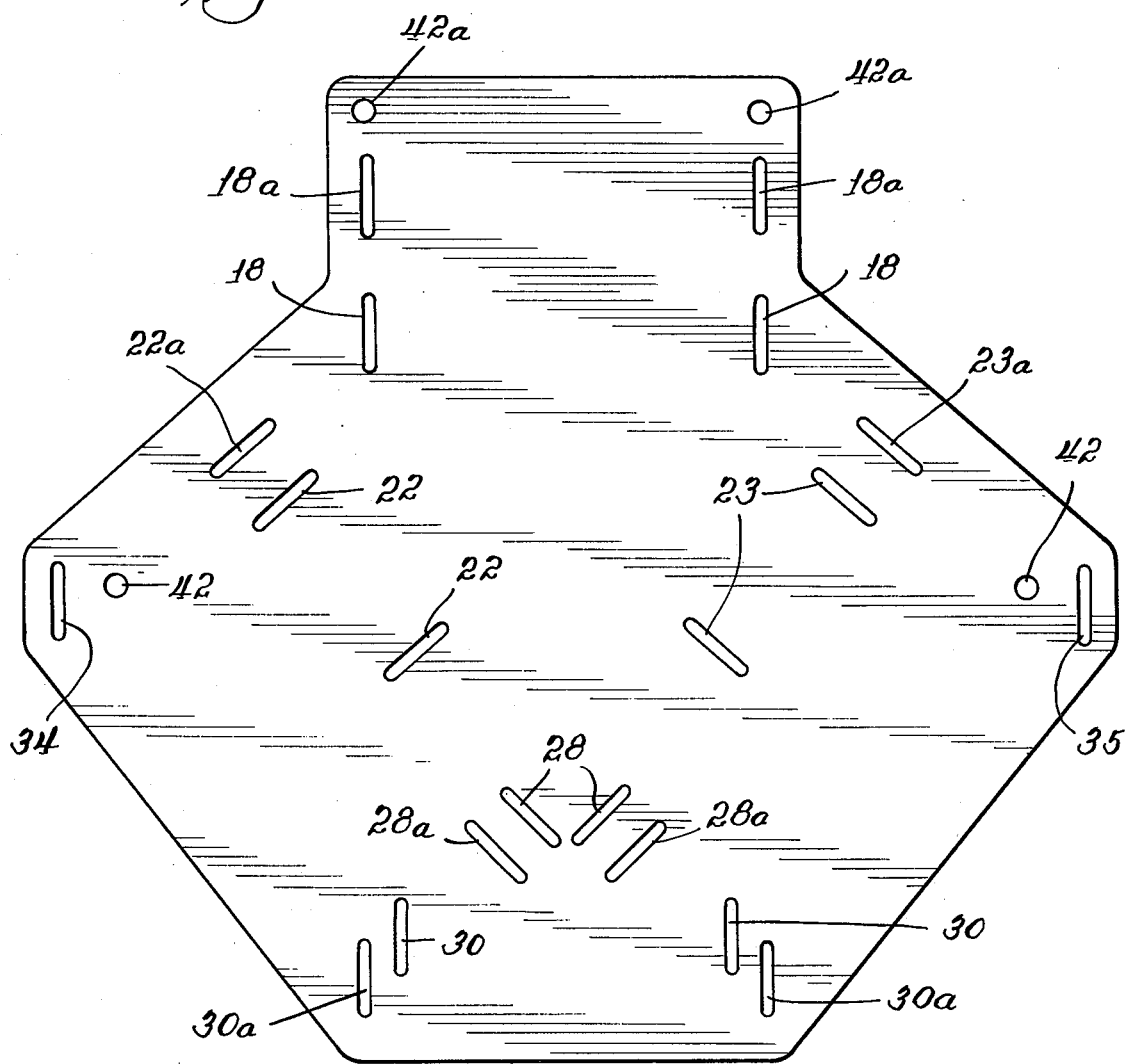

PATIENT RESTRAINT FOR X-RAY STUDIES OF INFANTS

BACKGROUND OF THE INVENTION

X-ray studies of congenital dislocation of the hip, and studies of abnormalities of the hips commonly require exposure of X-ray film while an infant or small child is in a straight supine position as well as in a so-called frog-leg position. The straight supine position, sometimes loosely referred to as the antero-posterior position, or as the "A-P" position, is intended to refer to the position of the patient when laying on his back, legs together, and outstretched in the plane of the body. By frog-leg position is meant the position in which the patient is on his back, thighs spread apart, with the femurs rotated outwardly by about a quarter turn, thus bringing the thighs and lower legs into the same plane as the body. The ankles are drawn back toward each other near a midline to assist in maintaining the rotated position of the femurs. The frog-leg position provides a front view of the pelvis and a lateral view of the head of the femur.

Because of the lack of cooperation available in babies and small children, it is usually necessary that an adult attempt to hold the young patient immobile while the film is being exposed for antero-posterior projection in frog-leg position. This necessarily involves inadvertent exposure of the non-patient adult to the risk of X-ray radiation. Moreover, because of the likelihood of shifting of position of the patient on the table itself, it is common practice to expose one 8 × 10 plate for each respective A-P and frog-leg position. Ordinarily the adult lays one hand on the chest or abdomen of the child, and, for the A-P position, holds the legs together just above the knees. In attempting to hold the child in the frog-leg position the adult usually places one hand on the chest or abdomen of the child and, with the other hand grasping the ankles of the child, attempts to maintain the thighs and legs in the outwardly disposed frog-leg configuration. This is quite difficult and if the child is crying or squirming it is quite common for one or the other thigh to be extended upward at a considerably different angle than the other during exposure of the film. Needless to say, this makes direct comparison of measurements taken of some of the child's anatomical structures on both sides of the body an exercise in futility.

Also, in taking cystograms of young patients, e.g. small children and babies, it is common practice to catheterize the patient, inject a radio opaque contrast dye through the catheter into the urinary bladder, and expose X-ray film at several time intervals. Because of the discomfort to the patient, the young patient usually resists the catheterization and must be restrained during the catheterization. The movement and presence of others in attempting to restrain the child increases the risk of loss of sterile conditions during the catheterization procedure. Just as there has been a long felt need for improving the immobilization of patients during X-ray hip studies as outlined above, there has also been a long felt need of immobilizing the young patient during the catheterization and other steps involved in preparing a cystogram.

This invention permits the convenient and relatively comfortable immobilization of a very young patient during X-ray studies in which the frog-leg position is used. Moreover, it is relatively convenient to immobilize the patient in an A-P position without removing the patient from the restraint. This invention permits the exposure of a greatly reduced portion of the body of the patient to X-ray radiation, and permits clear precise positioning of the image with the result that a greatly reduced quantity of X-ray film is required. Also, repeated exposures, because of improper positioning of the extremities and because of inadvertent movement of the patient, is virtually eliminated. This invention also greatly improves the procedure for preparing a baby or small child for a cystogram.

DESIGNATION OF THE DRAWINGS

FIG. 1 is a plan view of the restraint board showing the lowermost strap arranged for use with the patient in a straight supine position.

FIG. 2 is a plan view illustrating the use of the apparatus having the configuration of FIG. 1 with the patient in a straight supine position.

FIG. 3 is a plan view of the apparatus shown in FIG. 1, the lowermost strap being arranged for use in conjunction with the positioning of a patient in a frog-leg position.

FIG. 4 illustrates the use of the restraint in the configuration illustrated in FIG. 3 to maintain the patient in a frog-leg position.

FIG. 5 is a cross-sectional fragmentary view taken along the line 5—5 in FIG. 1.

FIG. 6 is a plan view of a restraint board having alternative provisions for straps for use with two ranges of size of patient.

DESCRIPTION OF PREFERRED EMBODIMENTS

The restraint (i.e., the means of restraint), of the invention, generally 10, includes board 12 and a plurality of body encircling restraint means which will be described in detail hereinafter. Board 12, in the illustrated embodiment, is provided with a plurality of pairs of slots for passing body-encircling straps therethrough. A midline 16 is indicated in FIG. 1 to illustrate that the locations of slots 14 are such that the two halves of board 12 formed by line 16 are symmetrical with respect to slot positions, the line of symmetry being midline 16.

The respective pairs of slots and restraint straps passing therethrough will be discussed in detail hereinafter in a sequence beginning with the uppermost members in FIG. 1 and continuing through to the lowermost members in FIG. 1.

Uppermost pair 18 of slots are positioned to permit abdomen strap 20 to extend more or less perpendicularly from the board to encircle the abdomen of the patient laying on board 12. Pairs 22 and 23 of slots are positioned so that thigh straps 25 and 26 can encircle the patient's thighs when straps 25 and 26 extend more or less vertically from the slots to the thighs. Pair 28 of slots are arranged in a V configuration near the midline, lines drawn through them converging approximately on the midline 16. It is noted that the upwardly and outwardly diverging orientation of slot pair 28 is such that the V lines formed by this pair of slots when extended upwardly and outwardly fall over slot pairs 22 and 23, the individual slots of pairs 22, 23 being more or less perpendicular or at least being biased across the extended lines.

Lowermost slot pair 30 is oriented approximately parallel to slot pair 18 and are spaced apart substantially the same distance as that between slot pair 18.

Slot pair 30 is located with the individual slots being substantially equidistant from midline 16 to permit body encircling strap 32 to encircle the patient's thighs, with the strap extending upwardly from board 12.

Optional, adjustable table straps 33, fitted respectively through slots 34, 35 includes hook means 37, 38 for positioning and securing of restraint 10 to X-ray table (not shown because conventional).

Vacuum cups 40 are preferably used for the purpose of securing restraint 10 to the X-ray table. Vacuum cups 40 are secured to board 12 by suitable fastening means, such as nuts 42, and screw posts 43 illustrated in FIG. 5. It is preferred that fastening means 42 be positioned along the outermost edges of board 12.

The restraint board shown in FIG. 6 is an alternative form which expands the use of the board by providing alternative slot patterns, to some extent interrelated, to adapt the board for use with two ranges of size of infant patient. In the plan view shown, the slots already described are designated by the same numerals employed in the description of the board of FIG. 1. The additional slots, which provide for the accommodation of the larger infant, are designated by numerals corresponding to those of the slots having similar functions in the restraining of the smaller size infant with the addition of the letter a.

The distance between the pairs of slots 18a and 30a is greater than the distance between slot pairs 18 and 30 to adapt the board to the greater length of the infant. The additional slots 22a and 23a are employed along with the respective inner slots 22 and 23 to accommodate the larger thighs of the larger infant and, for the frog-leg position, the slots 28a and 30a are used instead of the slots 28 and 30 to adapt the board to the longer legs of the larger infant.

The arrangement and manner of use of the several straps are the same in the use of the board of FIG. 6 as has been described with reference to the board of FIGS. 1 and 3.

USE OF INVENTION

With the straps in the approximate configuration shown in FIG. 1 the infant is placed in supine position on the board over the midline and abdominal restraint strap 20 is secured around the lower abdominal portion 50. Thigh straps 32 are then fastened around both thighs 52, the patient's legs 54 extending straight downwardly from the body. The hip region is thus immobilized to a sufficient degree to permit exposure of X-ray film for the antero-posterior projection. The patient, thus secured to the board, is positioned on the X-ray table at the precise position required. Restraint 10 is secured to the table using either table fastening means 32, 33 or rubber suction cups 40, or both, and the film is exposed.

After the A-P exposure is completed, thigh straps 32 are released and the patient's thighs are spread outwardly so that the thighs lay over the regions 60, 61 (FIG. 3) between the individual slots of slot pairs 22, 23. Thigh straps 25, 26 are then secured around the respective thighs of the patient and free end 65 of long thigh strap 32 is passed in and out through slot pair 28 by being first passed downwardly through slot designated 66 in FIG. 3, behind board 12, and upwardly through slot designated 67 in FIG. 3. Thus, loop 70 is formed by the passage of end 65 through slot 66. The infant's foot 72 at the infant's left is passed through loop 70, while loop 70 is relatively large. Loop 70 is positioned to encircle lower portion 74 of the infant's leg. Loop 70 can be drawn snugly and comfortably around leg portion 74 by pulling of strap 32 at region 75 at the underside of board 12 permitting snugging-up of loop 70. However, though free end 65 can be pulled easily through slot 67, loop 70 will not open any wider than the adjusted position in spite of vigorous pulling thereon because of the angular relationship of slots 66, 67, but more importantly because of the angular relationship between slots 66, 68 at either side of loop 70. The tenacity of this locking effect will, of course, depend somewhat on the magnitude of slots 66, 67, 68, but, in any event, portion 72 under loop 70 is relatively secure and little or no tension need be applied at free end 65 or at buckle end 37 of belt 32 in order to keep loop 70 secure. This frees both hands to continue work with the patient and eliminates the need for use of a fastening device for loops for both ankles. The other leg 78 of the patient is then rotated outwardly approximately a quarter of a turn and lower portion 79 is drawn toward midline 16 to permit lower portion 79 to lay across the region 80 between slot 67 and slot 81 from which buckle end 77 of belt 32 emerges. Free end 65 is then secured to buckle end 67 of belt 32 to encircle lower region 79 of leg 78 in the thus formed loop 83.

Thus, the illustrated preferred embodiment utilizes a slot arrangement which provides locking means for maintaining the adjustment of loop 70 while leg 78 is being properly secured. The patient, thus secured in frog-leg position illustrated in FIG. 4 is then accurately and virtually immovably secured over the precise position required for the exposure of X-ray film and exposure of X-ray film with the patient in the frog-leg position is easily and conveniently accomplished.

ACHIEVEMENT

By use of this invention it is no longer necessary to expose a relatively large region of the patient's body to X-ray radiation in order to compensate for possible inadvertent shifting or moving of the patient on the table between the time the patient is positioned and the time the X-ray technician exposes the film. It has been heretofore common practice to use a relatively large plate, e.g. 8 × 10 inches, for each exposure, and expose a relatively large region in order to preclude the necessity of re-exposing film should the patient be inadvertently moved or inadvertently move. In accordance with the use of this invention, not only is the problem relating to inadvertent patient shifting eliminated, but in addition the anatomical structures are fixed with respect to the film position. The necessity of re-exposure due to inadvertent movement of the patient during the exposure is virtually eliminated.

Moreover, because of the precise and dependable positioning which can be achieved using the apparatus and technique of this invention, a portion of a plate can be shielded to expose only a fractional portion of the plate, making it possible to prepare a film, e.g. 10 × 12 inches, having the full antero-posterior projection of both hips in straight supine position on one portion thereof and the full antero-posterior projection of both hips in frog-leg position on the adjacent portion of the same film. For example, side-by-side images are conveniently prepared in accordance with this invention using 10 × 12 inch plate, shielding half of the plate, i.e. exposing only a 6 × 10, inch portion of the plate, exposing the film with the radiation coned down to expose a relatively small region of the patient's body. After exposure of the first portion, the plate is shifted, and the position of the patient is changed to the frog-leg position as described above. The other portion of the plate is exposed with the patient in the frog-leg position immediately and precisely above the fresh film region. The result is two adjacent images, for example about four inches high and about six inches wide, showing the same patient in antero-posterior projection in straight supine position in one image and in frog-leg position in the other.

This side-by-side configuration reduces the number of films required and this is significant, not only from the cost of the film, but from the consideration of storage requirements. Moreover, because of the precise positioning which can be achieved, the use of relatively small plates is now possible. For example, strips of X-ray film approximately 4 × 12 inches can be used and processing of these smaller strips presents no problem whatsoever in most conventional automatic X-ray film processing equipment. Nonetheless, it represents a substantial saving in cost of relatively expensive X-ray film.

Restraint 10 is of great value in preparing small patients, male or female, for cystograms.

Use of suction cups 40 is preferred, and surprisingly enough, do not lead to substantial problems of sharpness because of the slight elevation of the child off the X-ray table. Board 12 can be plywood, fiberboard, or other material which permits passage of X-rays therethrough to a sufficient extent. Use of ⅛ inch fiberboard has been found to require no change in KV setting or exposure time to produce an image entirely comparable in contrast to that obtained without the board. Board 12 is preferably finished with a water, alcohol, and acetone resistant finish.

While the restraints shown herein utilize conventional buckles the invention is not limited to the use of such fasteners. Any conventional fastening means may be employed. The strap ends may be fastened together by means of pressing a felt-like panel fastened at one end of the strap to a hook panel, containing a multiplicity of tiny flexible plastic hooks, fixed to the other end of the strap. The latter mentioned conventional fastening means are available under the trademark VELCRO.

I claim:

1. An infant restraint particularly suitable for immobilizing an infant in either supine or frog-leg position during X-ray examination including:
    a panel having a vertical midline;
    first strap means near the top of said panel for encircling the lower abdomen of the infant;
    a first pair of vertical slots laterally spaced apart and equidistant from said midline for receiving said first strap means;
    second strap means near the bottom of said panel for encircling both thighs of the infant when said thighs are positioned next to each other;
    a second pair of vertical slots laterally spaced apart and equidistant from said midline for receiving said second strap means;
    third and fourth strap means respectively located above said second strap means for separately encircling the respective thighs of the infant when in frog-leg position;
    a third and a fourth pair of spaced slots for receiving said third and fourth strap means, respectively, said third and fourth pairs of slots being respectively oriented and positioned perpendicular to and laying along one of a pair of upwardly divergent lines crossing said midline at substantially the same juncture point; and
    a fifth pair of spaced slots arranged below said third and fourth pairs of slots adjacent said upwardly extending divergent lines and substantially parallel thereto;
    for receiving therethrough said second strap means to form ankle-restraining loops when the infant is in frog-leg position.

2. An infant restraint in accordance with claim 1 and including an additional pattern of slots adapting the panel for use with larger infants, said additional pattern comprising a second first pair of slots located above said first pair, a second second pair of slots located below said second pair, a third slot added to the third and fourth pairs and respectively located outwardly along the divergent lines, and a second fifth pair of slots located below said fifth pair.

3. In an infant restraint for immobilizing an infant in either straight supine or frog-leg position for X-ray examination including a panel having an abdomen-encircling strap fastened thereto in the upper portion thereof and a pair of spaced vertical slots in the lower portion thereof and a strap adapted to encircle the thighs of an infant in supine position upon said panel passing through said vertical slots, the improvement which comprises:
    two straps arranged respectively to encircle the respective thighs of an infant patient upon the panel in frog-leg position and means for fastening said straps to the panel, and
    a pair of upwardly diverging slots spaced equidistant laterally from the vertical center line of the panel and located above and inwardly from the vertical slots in the lower portion of the panel,
    whereby the strap adapted to encircle the thighs of an infant when in supine position is adapted when passing successively through the outermost slots of said vertical and divergent pairs of slots to encircle the lower portions of the legs of the infant when in frog-leg position.

* * * * *